(12) United States Patent
Hameyer et al.

(10) Patent No.: US 8,795,692 B2
(45) Date of Patent: Aug. 5, 2014

(54) COLD-PREPARABLE, LOW-VISCOSITY AND PROLONGED-STABILITY COSMETIC EMULSIONS

(75) Inventors: Peter Hameyer, Essen (DE); Jürgen Meyer, Münster (DE); Gabriele Polak, Hagen (DE)

(73) Assignee: Evonik Degussa GmbH, Essen (DE)

( * ) Notice: Subject to any disclaimer, the term of this patent is extended or adjusted under 35 U.S.C. 154(b) by 1779 days.

(21) Appl. No.: 11/657,265

(22) Filed: Jan. 24, 2007

(65) Prior Publication Data

US 2007/0178144 A1 Aug. 2, 2007

(30) Foreign Application Priority Data

Jan. 30, 2006 (DE) .................. 10 2006 004 353

(51) Int. Cl.
| | |
|---|---|
| A61Q 19/00 | (2006.01) |
| A61K 8/06 | (2006.01) |
| A61K 8/37 | (2006.01) |
| C11D 17/00 | (2006.01) |
| A61K 8/02 | (2006.01) |

(52) U.S. Cl.
CPC .......... *A61Q 19/00* (2013.01); *A61K 8/062* (2013.01); *A61K 8/068* (2013.01); *A61K 8/37* (2013.01); *A61K 8/0208* (2013.01); *C11D 17/0017* (2013.01); *C11D 17/0021* (2013.01); *C11D 17/0043* (2013.01)
USPC .......... 424/401; 424/443; 510/157; 510/159; 510/417

(58) Field of Classification Search
CPC ................................. A61Q 19/00
See application file for complete search history.

(56) References Cited

U.S. PATENT DOCUMENTS

| | | | |
|---|---|---|---|
| 4,931,210 A | 6/1990 | Takahashi et al. | |
| 5,599,827 A | 2/1997 | Gironda | |
| 5,876,702 A | 3/1999 | Gers-Barlag et al. | |
| 6,066,328 A | 5/2000 | Ribier et al. | |
| 6,562,876 B1 * | 5/2003 | Ansmann et al. | 516/77 |
| 7,658,936 B2 | 2/2010 | Von Der Fecht et al. | |
| 2002/0146375 A1 | 10/2002 | Schreiber et al. | |
| 2004/0105828 A1 * | 6/2004 | Chaiyawat et al. | 424/63 |
| 2005/0002994 A1 * | 1/2005 | Goppel et al. | 424/443 |
| 2005/0025957 A1 | 2/2005 | Issberner et al. | |
| 2005/0287104 A1 | 12/2005 | Aubrun-Sonneville et al. | |
| 2009/0130153 A1 | 5/2009 | Issberner et al. | |
| 2009/0131542 A1 | 5/2009 | Issberner et al. | |

FOREIGN PATENT DOCUMENTS

| | | | |
|---|---|---|---|
| DE | 19548016 A1 | | 6/1997 |
| DE | 19726121 A1 | | 12/1998 |
| DE | 19859427 A1 | | 6/2000 |
| DE | 10129973 A1 | | 1/2003 |
| DE | 10334225 A1 | | 2/2005 |
| DE | 102005011785 | | 9/2006 |
| EP | 0387647 A2 | | 9/1990 |
| EP | 0745324 A1 | | 12/1996 |
| EP | 1092414 A2 | | 4/2001 |
| EP | 1268740 | | 5/2004 |
| JP | 2001-081024 | * | 3/2001 |
| WO | 00/04230 | | 1/2000 |
| WO | 02/056841 | | 7/2002 |
| WO | WO02056843 A2 | | 7/2002 |
| WO | WO02080864 A1 | | 10/2002 |

OTHER PUBLICATIONS

Smolinske, S.C. (1992). Handbook of food, drug and cosmetic excipients. CRC Press. Accessible online at: http://books.google.com/books?id=FDisTRAhLRoC&printsec=frontcover&source=gbs_navlinks_s#v=onepage&q=&f=false.*
Machine translation of JP 2001-081024 (2001).*
Shinoda, Kozo et al. "Phase Properties of Emulsions: PIT and HLB", Emuslions, Microemulsions, and Solubilization, 1979, pp. 337-367.
Förster, Th. et al., "Production of Fine Disperse and Long-Term Stable Oil-In-Water Emulsions by the Phase Inversion Temperature Method", J. Dispersion Science and Technology, 1992, pp. 183-193, vol. 13, No. 2.
Elvers, Barbara et al., "Ullmann's Encyclopedia of Industrial Chemistry", Fifth, Completely Revised Edition, vol. B7, Environmental Protection and Industrial Safety I, 1995.
European Search Report dated May 25, 2010.

* cited by examiner

*Primary Examiner* — Daniel Sullivan
*Assistant Examiner* — Barbara Frazier
(74) *Attorney, Agent, or Firm* — Scully, Scott, Murphy & Presser, P.C.

(57) ABSTRACT

PEG-free, cold-preparable, prolonged-stability, low-viscosity, fine oil-in-water emulsions, their preparation from preferably clear oil phases or via preferably clear to transparent microemulsion-like concentrates, the corresponding oil phases or microemulsion-like concentrates and the use of the inventive emulsions for producing cosmetic, dermatological, pharmaceutical or industrial formulations, especially for the production of impregnating emulsions for wet wipes or for sprayable care emulsions are provided.

16 Claims, No Drawings

COLD-PREPARABLE, LOW-VISCOSITY AND PROLONGED-STABILITY COSMETIC EMULSIONS

FIELD OF THE INVENTION

The present invention relates to emulsions, and more particularly to cold-preparable, prolonged-stability, low-viscosity, fine oil-in-water emulsions, their preparation from preferably clear oil phases or via preferably clear to transparent microemulsion-like concentrates, and the corresponding oil phases or microemulsion-like concentrates. The present invention also relates to the use of the inventive emulsions for producing cosmetic, dermatological or pharmaceutical formulations, and for the production of cleaning and care emulsions for the household and industry, especially for the production of impregnating emulsions for wet wipes or for sprayable care emulsions.

BACKGROUND OF THE INVENTION

Emulsions constitute an important product type in the field of cosmetic, dermatological and/or pharmaceutical formulations. Cosmetic formulations are utilized essentially for skincare. Skincare, in the cosmetic sense, is primarily the enhancement and/or reestablishment of the natural function of the skin as a barrier against environmental influences (for example, soil, chemicals, microorganisms, etc.) and against the loss of endogenous substances (for example, water, natural fats, electrolytes, etc.).

A further aim of skincare is to compensate for the loss of fats and water in the skin caused by daily washing and to preserve and restore the softness and smoothness of the skin. This is important when the natural regeneration capacity is insufficient. Moreover, skincare products should provide protection from environmental influences, especially from the sun and the wind, and delay skin ageing.

Pharmaceutical topical compositions generally comprise one or more medicaments in an effective concentration. For the sake of simplicity, cosmetic and medical use and corresponding products are clearly distinguished by reference to the legal stipulations of the Federal Republic of Germany (for example, Cosmetics Act, Food and Drug Laws).

In the last few years, cosmetic wet wipes have gained increasing significance owing to their extremely simple and convenient usability. Initially, virtually exclusively wet wipes for cleaning purposes were represented on the cosmetics market, which comprised mainly aqueous, surfactant-containing impregnating solutions. However, in recent times, care products have also been appearing more and more on the market, which are based on impregnating emulsions and thus additionally comprise a care oil component.

Most of these cosmetic wet wipes for bodycare and facecare are impregnated with emulsions which have been prepared by the PIT emulsifying method (see, for example, K. Shinoda, H. Kunieda, Phase properties of emulsions: PIT and HLB, Encycl. of Emulsion Technology, 337-367 (1), 1983 or Th. Förster, F. Schambil, W. von Rybinski, J. Disp. Sci. And Technology, 13(2), 183-93 (1992)).

The PIT method makes use of the fact that, in an oil-in-water (O/W) emulsion which is stabilized by nonionic emulsifiers containing polyethylene glycol ("PEG-containing emulsifiers"), a phase inversion can be induced to give a water-in-oil (W/O) emulsion by increasing the temperature (phase inversion; PIT: phase inversion temperature).

Since the water-oil interface tension is extremely low in this phase inversion region, extremely fine oil-in-water emulsions can thus be obtained after cooling. For this purpose, it is, however, necessary that the individual components of the emulsions are adjusted precisely with respect to one another for each system to be emulsified. This means that emulsifier mixtures and emulsifier concentration have to be "tailored" for different oil phases.

The fine and low-viscosity emulsions thus produced have excellent long-term stability and are thus very suitable as impregnating solutions for wet wipes. Such systems are described, for example, in EP-B-1 268 740 or WO-A-00/04230.

A fundamental requirement for the use of PIT emulsification technology is, as described, the necessity for the entire emulsion to be heated to temperatures above the phase inversion temperature and thereafter to be cooled down.

At the present time, where process operations have to be optimized and energy costs restricted, this means a distinct disadvantage compared to systems which do not have to pass through this heating/cooling curve. For this reason, fine, prolonged-stability emulsions which can be prepared at room temperature ("cold preparation") without having to pass through an additional heating/cooling curve would be advantageous.

Another disadvantage in impregnating solutions for wet wipes based on PIT emulsions is that such wet wipes are based on the use of PEG-containing emulsifiers. In view of very natural cosmetic formulations, it is an important aim of cosmetic research to be able to dispense with emulsifiers containing polyethylene glycol ("PEG"). There is therefore an increased search for PEG-free alternative solutions.

It is also known that ethoxylated emulsifiers impart a rather watery skin feel, which can be improved sensorily by the use of, for example, polyglyceryl esters.

For instance, WO-A-02/056841 describes PEG-free impregnating emulsions for cosmetic wet wipes based on polyol poly-12-hydroxystearates and alkyl glycosides. The use of these emulsifier mixtures leads to improved softness of paper products impregnated with them and also leads to improved sensory properties in use of the wet wipes produced with them. In the case of such emulsifier combinations, it is, however, generally difficult to achieve good long-term stability of the impregnating emulsions in combination with sufficient preservation.

Especially in the production of wet wipes, sufficient preservation of the impregnating solutions is absolutely necessary in order to prevent germ growth. The preservation has to be sufficient to protect both the impregnating solutions themselves and finally also the impregnated wet wipes in the long term against germ growth.

Preferred preservative mixtures used are typically mixtures of alkylparaben esters and phenoxyethanol, as are commercially available, for instance, under the trade names Euxyl® K 300 (Schülke & Mayr) or Phenonip® (Clariant).

The described requirements regarding reliable preservation of impregnating solution and wet wipes make it necessary that relatively large amounts of these alkylparaben ester/phenoxyethanol mixtures generally have to be used in the finished impregnating solutions (0.5 to 1.0% by weight). Ideally, the entire amount of preservative should be incorporated as early as in the production of emulsion concentrates as possible. This allows the desired use concentration of the impregnating solution to be established subsequently in a simple manner by dilution with water.

It is known that the use of these alkylparaben ester/phenoxyethanol mixtures has an emulsion-stressing influence, since these compounds are very interface-active and compete with emulsifier molecules for a space at the oil-water interface. Owing to the interface-active character of these preservative mixtures, they can therefore also be described as aromatic cosurfactants with preservative properties. In the case of impregnating emulsions for wet wipes, this emulsion-stressing effect is generally enhanced by the required high amounts of these preservatives and the low viscosities of the impregnating solutions.

In summary, it can therefore be stated that it is not possible with the emulsifiers or emulsifier combinations described in the prior art to prepare cold-preparable, sufficiently preserved, low-viscosity, fine and prolonged-stability emulsions, as are typically used for impregnating emulsions or sprayable lotions.

SUMMARY OF THE INVENTION

The present invention provides a technique for preparing low-viscosity, fine and prolonged-stability emulsions, as used typically for impregnating emulsions or sprayable lotions, i.e., which simultaneously can be prepared at room temperature,
are free of ethoxylated constituents, and
which additionally contain a sufficient amount of preservative compounds.

It has now been surprisingly found that low-viscosity, fine and prolonged-stability oil-in-water emulsions, which are outstandingly suitable for use as impregnating emulsions or in sprayable systems, are preparable at room temperature when a suitable combination of emulsifiers based on polyol partial esters and neutralizable acid partial esters is used together with oils, preferably ester and/or ether oils and cosurfactants, preferably aromatic cosurfactants with preservative properties.

In addition to their ease of preparation and their fine dispersion, these emulsions are notable in that they are essentially free of ethoxylated ingredients ("PEG-free" emulsion systems). The wet wipes produced with the aid of these impregnating solutions are additionally notable for exceedingly pleasant sensory properties.

The inventive oil-in-water emulsions provide for the first time PEG-free, low-viscosity and fine emulsions which are preparable at room temperature and are simultaneously sufficiently preserved and have prolonged stability by virtue of the use, preferred in accordance with the invention, of preservation-active aromatic cosurfactants, and are thus suitable in particular for use as impregnating emulsions for wet wipes.

The invention therefore provides prolonged-stability, low-viscosity, fine oil-in-water emulsions comprising:
A) an emulsifier mixture consisting of:
a) at least one nonionic primary emulsifier, and
b) at least one secondary emulsifier containing one or more acid functions, all or some of which may optionally be neutralized;
B) one or more cosurfactants;
C) one or more oils;
D) optionally, one or more polar solubilizers; and
E) optionally, customary assistants and additives,
with the proviso that the water phase content of the emulsions is ≥80% by weight based on the overall emulsion.

Emulsions preferred in accordance with the invention have low viscosity, are finely distributed and have long-term stability.

"Low viscosity" is understood to mean a viscosity which enables spraying of the emulsions with a customary apparatus. In general, these are emulsion viscosities of ≤4000 mPas (Brookfield RVT, spindle 4, 10 rpm (20° C.)), preferably ≤2500 mPas, more preferably ≤1000 mPas. Higher viscosities are attainable, but are not preferred in accordance with the invention.

The term "fine" is used in the present invention to denote a mean radius of the emulsion droplets of ≥20-≤500 nm, preferably of ≥30-≤200 nm, and more preferably of ≥40-≤120 nm.

"Prolonged stability" is understood to mean that the inventive emulsions can be stored for three months at room temperature and for 1 month at 40° C. without irreversible creaming or other signs of instability.

DETAILED DESCRIPTION OF THE INVENTION

As stated above, the present invention provides prolonged-stability, low-viscosity, fine oil-in-water emulsions which include:
A) an emulsifier mixture consisting of:
a) at least one nonionic primary emulsifier, and
b) at least one secondary emulsifier containing one or more acid functions, all or some of which may optionally be neutralized;
B) one or more cosurfactants; and
C) one or more oils,
with the proviso that the water phase content of the emulsions is ≥80% by weight based on the overall emulsion.

In some embodiments of the present invention, the inventive oil-in-water emulsions may, but not necessarily, include, as optional components:
D) one or more polar solubilizers; and
E) customary assistants and additives.

The inventive oil-in-water emulsions typically have a water phase content of ≥70-≤99% by weight, preferably of ≥80-≤97% by weight.

The water phase includes all substances in a formulation which are added to this phase or can be dissolved or dispersed in it owing to their hydrophilic character. Based on the inventive oil-in-water emulsions, water or any constituents such as glycols, polyalkylene glycols, glycerol, polyglycerols, alcohols, water-soluble polymers or active ingredients in any case belong to the water phase.

In all aspects of the invention, the emulsifier mixture (A), the cosurfactants (B) and the oils (C) are used preferably in proportions by weight (based on these three components) of (A) ≥10-≤30, (B) ≥3-≤20, (C) ≥50-≤87, and more preferably in proportions by weight of (A) ≥20-≤25, (B) ≥5-≤15, (C) ≥60-≤75, the emulsifier mixture (A) being composed of ≥75-≤99.5% by weight of nonionic primary emulsifier (a) and ≥0.5-≤25% by weight of secondary emulsifier (b) containing acid groups.

For the emulsifier mixture (A), preference is given in accordance with the invention to using, for the nonionic primary emulsifiers (a), polyol partial esters selected from at least one of the groups of:
a1) glyceryl and polyglyceryl partial esters, preferably prepared by esterifying aliphatic, linear or branched, optionally unsaturated and/or hydroxy-functionalized carboxylic acids having a chain length of from ≥6 to ≤22 carbon atoms with glycerol, polyglycerols or mixtures of the two,
a2) sorbitan or sorbitol partial esters, preferably prepared by esterifying aliphatic, linear or branched, optionally unsaturated and/or hydroxy-functionalized carboxylic acids having a chain length of from ≥6 to ≤22 carbon atoms with sorbitol,
a3) carbohydrate esters, preferably glycoside or sucrose esters, preferably prepared by esterifying aliphatic, linear or branched, optionally unsaturated and/or hydroxy-functionalized carboxylic acids having a chain length of from ≥6 to ≤22 carbon atoms with mono- or polysaccharides, and optionally higher saccharides, a4) (alkylpoly)glycosides, preferably prepared by reacting aliphatic, linear or branched, optionally unsaturated and/or additionally hydroxy-functionalized alcohols having a chain length of from ≥6 to ≤22 carbon atoms with mono- or polysaccharides, or mixtures thereof.

Typically, the main part of the nonionic primary emulsifier component (a) consists of polyglyceryl esters, to which sorbitan esters have preferably been added in an amount of ≥0-≤75% by weight, preferably ≥0-≤50% by weight, more preferably ≥0-≤25% by weight, based on overall primary emulsifier component (a).

Preference is given to polyglyceryl partial esters and sorbitan partial esters which contain, as hydrophobic moieties, fatty acid radicals having a chain length of from ≥10 to ≤18 carbon atoms.

Very particular preference is given to a combination of polyglyceryl laurates and sorbitan laurates.

For the emulsifier mixture (A), preference is given, for the secondary emulsifier component (b), to compounds selected from at least one of the groups of:

b1) optionally hydroxyl-containing di- or polycarboxylates, sulfated, sulfonated or phosphated carboxylates, malonates, malates, succinates, sulfosuccinates, citrates, tartrates, in each of which some of the acid groups have been esterified with aliphatic or aromatic, linear or branched, optionally unsaturated and/or hydroxy-functionalized alcohols having a chain length of from ≥6 to ≤22 carbon atoms, b2) optionally hydroxyl-containing di- or polycarboxylates, sulfated or sulfonated or phosphated carboxylates, malonates, malates, succinates, sulfosuccinates, citrates, tartrates, in each of which some of the acid groups have been esterified with polyols, polyol partial esters, preferably formed from glycerol, polyglycerol and/or sorbitol with aliphatic or aromatic, linear or branched, optionally unsaturated and/or hydroxy-functionalized carboxylic acids having a chain length of from ≥6 to ≤22 carbon atoms, b3) polyols, preferably glycerol, polyglycerol and sorbitol, which have been partly esterified with aliphatic or aromatic, linear or branched, optionally unsaturated and/or hydroxy-functionalized mono-, di- or polycarboxylic acids having a chain length of from ≥2 to ≤22 carbon atoms, with the proviso that free, neutralizable acid groups are present in the molecule, b4) hydroxy-functional mono-, di- or polycarboxylic acids, at least some of whose hydroxyl groups have been reacted with aliphatic, linear or branched, optionally unsaturated and/or hydroxy-functionalized carboxylic acids having a chain length of from ≥6 to ≤22 carbon atoms, b5) N-acyl amino acids such as sarcosinates, glutamates, aspartates, containing an aliphatic or aromatic, linear or branched, optionally unsaturated and/or hydroxy-functionalized radical having a chain length of from ≥6 to ≤22 carbon atoms, b6) carboxylates, sulfates, sulfonates, phosphonates or phosphates, containing an aliphatic or aromatic, linear or branched, optionally unsaturated and/or hydroxy-functionalized acyl radical having a chain length of from ≥6 to ≤22 carbon atoms, or mixtures thereof.

The emulsifiers of type (b) are present in the emulsifier formulation preferably in at least partly neutralized form. The emulsifiers of type (b) are advantageously used already as (partly) neutralized components. If desired, the neutralization step can also be effected in a later processing step, in which case the bases used for the neutralization are preferably those which lead to anion-active emulsifiers with mono- or divalent cationic counterions. Particularly preferred counterions are sodium and potassium.

Preference is given to using neutralized citric acid partial esters whose hydrophobic radicals each contain from ≥10 to ≤18 carbon atoms.

Very particular preference is given to the partial esters of citric acid and lauryl alcohol or of citric acid and glyceryl mono- or dilaurates, and also to partial esters of citric acid and oleyl alcohol or citric acid and glyceryl mono- or dioleates.

In the context of the present invention, cosurfactants are understood to mean those compounds which feature interface activity, which can be manifested in the lowering of interface tensions or the incorporation into interface films, but without these substances taken alone exhibiting the aggregation typical of surfactants to give micellar structures in water or the stabilization typical of emulsifiers for emulsion droplets.

In the context of the present invention, cosurfactants are additionally or alternatively understood to mean those compounds which have a HLB value according to Griffin of between ≥4 and ≤10. These cosurfactants more preferably feature an octanol-water partition coefficient log P or log $K_{ow}$ which is between 1 and 2. The octanol-water partition coefficient is calculated from the decadic logarithm of the quotient of the amount of a substance dissolved in octanol and in water in equilibrium at room temperature (see: Ullmann's Encyclopedia of Industrial Chemistry, Volume B 7, (Volume Editor: E. Weise), $5^{th}$ edition, VCH, Weinheim 1995, P. 78).

Advantageously, the inventive cosurfactants are nonionic organic compounds which have from 4 to 14 carbon atoms and one or more polar groups in the molecule.

Typical known nonaromatic cosurfactants are aliphatic alcohols such as butanol, pentanol, hexanol, octanol, hexanediol or octanediol. In a preferred embodiment of the invention, the cosurfactants used are n-pentanol, n-hexanol, 1,2-hexanediol, 1,2-heptanediol or 1,2-octanediol.

In addition, the cosurfactants used are preferably monoalkyl ethers or monoalkyl esters based on glycerol, ethylene glycol, propylene glycol or diethylene glycol with fatty acids or alcohols having from 6 to 10 carbon atoms.

In a preferred embodiment of the invention, the cosurfactants used are aromatic cosurfactants. In the context of the present invention, aromatic cosurfactants are understood to mean interface-active substances which contain one or more aryl groups and which, taken alone, do not form any micellar structures in water.

Advantageously, these aromatic cosurfactants additionally feature antimicrobial properties, i.e., they are aromatic cosurfactants with preservative properties. The use of such cosurfactants enables the preparation of inventive O/W emulsions which ideally need no further preservatives. In addition, it is of course possible to add further customary preservatives (as assistants and additives), as described, for instance, in DE102005011785.6.

Aromatic cosurfactants which have preservative properties and are particularly preferred in accordance with the invention are phenoxyethanol and benzyl alcohol, alone or in combination with one or more alkylparaben esters, preferably methylparaben, ethylparaben, propylparaben, isopropylparaben, butylparaben and/or isobutylparaben. Particular preference is given to the use of mixtures of alkylparaben esters and phenoxyethanol, as are commercially available under the trade names Euxyl® K 300 (Schülke & Mayr) or Phenonip® (Clariant).

As mentioned, it is also possible to use mixtures of preservation-active aromatic cosurfactants with other suitable preservatives. For example, it is also possible to use a mixture of phenoxyethanol and ethylhexyl glycerol, as is commercially available under the name Euxyl PE 9010 (Schülke & Mayr).

In the context of the present invention, oils are understood to mean compounds selected from the group of Guerbet alcohols based on fatty alcohols having from 6 to 20, preferably from 8 to 10 carbon atoms, esters of linear C1-C44-fatty acids with linear C1-C22-fatty alcohols, esters of branched C1-C44-carboxylic acids with linear C1-C22-fatty alcohols, esters of linear C1-C44-fatty acids with branched alcohols, esters of linear and/or branched fatty acids with polyhydric alcohols and/or Guerbet alcohols, triglycerides based on C1-C44-fatty acids, vegetable oils, branched primary alcohols, substituted cyclohexanes, Guerbet carbonates, dialkyl(ene) ethers, dialkyl(ene) carbonates and/or aliphatic or naphthenic hydrocarbons, silicone oils, dimethicones, cyclomethicones, ethoxylated and/or propoxylated organic alcohols, ethoxylated and/or propoxylated organic acids or mixtures thereof. Perfume oils known to those skilled in the art may also serve as the oil phases in the context of the invention.

In a preferred embodiment of the invention, the oils used are ester oils, ether-based oils, hydrocarbons and propoxylated organic alcohols, and mixtures of these compounds.

Useful ester oils include, but are not limited to, mono- or diesters of linear and/or branched mono- and/or dicarboxylic acids having from ≥2 to ≤44 carbon atoms with linear and/or branched (especially 2-ethylhexanol), saturated or unsaturated alcohols having from ≥1 to ≤22 carbon atoms. Likewise suitable in the inventive context are the esterification products of aliphatic, difunctional or trifunctional alcohols (especially dimer diol and/or trimer diol) having from ≥2 to ≤36 carbon atoms with one or more monofunctional aliphatic carboxylic acids having from ≥1 to ≤22 carbon atoms. Also suitable in accordance with the invention are ester oils which contain aromatic groups.

The partial use of ester oils which have waxy character at room temperature, for instance myristyl myristate, can lead to a richer skin feel of the emulsions.

Useful ether oils are, in particular, dialkyl ethers having from ≥4 to ≤24 carbon atoms. Particularly suitable in accordance with the invention are saturated C6-C18-dialkyl ethers, for example di-n-octyl ether, di(2-ethylhexyl)ether, lauryl methyl ether or octyl butyl ether, and also didodecyl ether.

Particularly preferred oil components are the cosmetic ester oils ethylhexyl palmitate, ethylhexyl stearate, decyl cocoate, diethylhexyl carbonate, dioctyl carbonate, cetearyl ethylhexanoate, decyl oleate, isocetyl palmitate, cetearyl isononanoate, hexyl laurate, isopropyl isononanoate, isopropyl palmitate, isopropyl myristate, isopropyl laurate and C12-15 alkyl benzoate, and the cosmetic ether oil dicaprylyl ether, and the propoxylated organic alcohols PPG15 stearyl ether or PPG-4 butyl ether, and mixtures of the compounds mentioned.

In the context of the present invention, "polar solubilizers" are understood to mean polar compounds which are added in amounts of up to 10% by weight to the oil phases described below in order to obtain clear oil phases. Polar solubilizers are preferably water, glycols, polyalkylene glycols, glycerol, polyglycerol or short-chain alcohols such as ethanol or isopropanol.

The assistants and additives used include all assistants and additives which are well known to a person skilled in the art, such as oils and waxes, commercial surfactants or emulsifiers, bodying agents, thickeners, for example, based on polymer, inorganic and organic UV light protection filters, self-tanning agents, pigments, antioxidants, hydrotropes, active deodorant and antiperspirant ingredients, other active ingredients, dyes, additional preservatives and perfumes, as described, for instance, in DE102005011785.6.

The assistants and additives may be added either to the oil or to the water phase, or to the diluent water in the preparation process of the emulsion.

Prefered active ingredients are, in particular, tocopherol, tocopherol acetate, tocopherol palmitate, ascorbic acid, deoxyribonucleic acid, coenzyme Q10, retinol and retinyl derivatives, bisabolol, allantoin, phytantriol, panthenol, AHA acids, amino acids, hyaluronic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolyzates, plant extracts and vitamin complexes.

The inventive O/W emulsions is typically prepared utilizing a simple stirrer apparatus. No additional homogenization step is required.

The preparation is preferably effected at room temperature by directly pouring a clear, monophasic oil phase comprising an emulsifier mixture, cosurfactants, oils and optionally customary assistants and additives into diluent water. If necessary, the oil phase may be converted to a clear phase by adding up to 10% by weight of a polar solubilizer. Such polar solubilizers may be water, glycols, polyalkylene glycols, glycerol, polyglycerols or short-chain alcohols such as ethanol or isopropanol. The polar solubilizer used is preferably water.

Homogeneous, clear oil phases are advantageous for the preparation of inventive fine O/W emulsions. The use of cloudy oil phases leads generally to relatively coarse emulsions whose long-term stability is often insufficient. The transition from clear to cloudy oil phases is fluid. The opacity at which emulsions with sufficient long-term stability can be prepared is dependent upon the type and amount of the components used and should be determined individually in these limiting cases.

Alternatively to the method mentioned, inventive fine oil-in-water emulsions can also be effected via the intermediate stage of a clear to transparent microemulsion-like concentrate. This concentrate consists generally of >30-≤90% by weight of oil phase, preferably of ≥40-≤80% by weight of oil phase, comprising an emulsifier mixture, cosurfactants, oils and optionally polar solubilizers and/or customary assistants and additives. These clear to transparent microemulsion-like concentrates are preferably prepared at room temperature by stirring water into the oil phase. To prepare these concentrates, it is also possible to use cloudy oil phases. The optimal water content of the concentrates is formulation-dependent (for example, on the oil used), but is generally ≥10-<70% by weight, preferably ≥20-≤60% by weight.

These microemulsion-like concentrates may finally be diluted to give inventive oil-in-water emulsions. Both the preparation of the microemulsion-like concentrates and the final dilution step can be effected at room temperature using a simple stirrer apparatus.

The invention therefore further provides oil phases comprising:
A) an emulsifier mixture consisting of:
a) at least one nonionic primary emulsifier, and
b) at least one secondary emulsifier containing one or more acid functions, all or some of which may optionally be neutralized;
B) one or more cosurfactants;

C) one or more oils;

D) from ≥0 to <10% by weight (based on the overall oil phase) of one or more polar solubilizers; and E) optionally customary assistants and additives.

Preference is given in accordance with the invention to homogeneous and clear oil phases.

These oil phases can be prepared by the known prior art processes. For example, the oil phases, depending on the consistency and concentration of the components used, can be prepared by simply mixing the components at temperatures in the range of ≥20 to ≤75° C. These oil phases can be used at room temperature to prepare the inventive oil-in-water emulsions.

The invention further provides a process for preparing the inventive oil-in-water emulsions, wherein these clear oil phases are preferably adjusted to a total water phase content of ≥70% by weight, preferably ≥80% by weight, at temperatures of less than 40° C., especially room temperature, with an appropriate water phase under conditions known per se.

The invention further provides clear to transparent microemulsion-like concentrates comprising:

A) an emulsifier mixture consisting of:
a) at least one nonionic primary emulsifier, and
b) at least one secondary emulsifier containing one or more acid functions, all or some of which may optionally be neutralized;

B) one or more cosurfactants;

C) one or more oils;

D) optionally, one or more polar solubilizers; and

E) optionally, customary assistants and additives, with the proviso that the total water phase content of the microemulsion-like concentrates is from ≥10 to <70% by weight, based on the overall concentrate.

The invention further provides a process for preparing the inventive oil-in-water emulsions, wherein these microemulsion-like concentrates are preferably adjusted to a total water phase content of ≥70% by weight, preferably ≥80% by weight, at temperatures of less than 40° C., especially room temperature, with an appropriate water phase under conditions known per se.

The invention further provides for the use of the inventive emulsions for producing cosmetic, dermatological or pharmaceutical formulations. In particular, the use as impregnating solutions for producing wet wipes, very particularly cosmetic wet wipes for the care and cleaning of the skin, are at the forefront.

The invention further provides for the use of the emulsions in cosmetic cleaning and care formulations for skin and skin appendages. In particular, the use in sprayable formulations is at the forefront, as used, for instance, for facecare and bodycare products, babycare, sun protection preparations, makeup removers and antiperspirants/deodorants.

The inventive oil-in-water emulsions are also outstandingly suitable both for the production of cleaning and care wet wipes and for direct use in the form of sprayable emulsion systems for the cleaning and care of surfaces in the household and industry, for example, textile care, leather care, the care and cleaning of metallic or nonmetallic surfaces, for example, for the cleaning and care of automobiles or furniture.

The invention accordingly further provides for the use of the emulsions for producing cleaning compositions and care compositions for the household and industry, such as textiles, leather, plastics, metallic and nonmetallic surfaces. In particular, the use as impregnating solutions for producing wet wipes and the use in sprayable formulations are at the forefront.

The technical teaching described here enables, in a simple manner, the preparation at room temperature of PEG-free, low-viscosity, fine and prolonged-stability oil-in-water emulsions which already have sufficient preservation.

The examples which follow are intended to illustrate the subject matter of the invention in detail without restricting it to these examples.

The concentrations in all examples are reported as % by weight.

The inventive oil phases, the inventive microemulsion-like concentrates and the inventive emulsions were prepared using a simple manual stirrer apparatus. After the corresponding oil phases had been prepared, both the conversion to inventive microemulsion-like concentrates and to inventive oil-in-water emulsions were effected at temperatures of <30° C.

In the case of preparation of the emulsions, it is advantageous to use the acid partial esters (b) used as part of the emulsifier mixture at least in partly neutralized form from the start. However, it is also possible to perform this neutralization step at a later point in the preparation process and initially to work with the non-neutralized acid partial esters.

In the examples, the acid partial esters used were used in neutralized form.

Example Emulsifiers 1-11:

Description of the emulsifier systems used in the example formulations (the total percentages (by weight) per emulsifier system in each case add up to 100):

| Emulsifier 1: | |
| --- | --- |
| Emulsifier component A: | 97% polyglyceryl-4 laurate[1] |
| Emulsifier component B: | 3% dilauryl citrate[2] |
| Emulsifier 2: | |
| Emulsifier component A: | 96% polyglyceryl-4 laurate[1] |
| Emulsifier component B: | 4% dilauryl citrate[2] |
| Emulsifier 3: | |
| Emulsifier component A: | 95% polyglyceryl-4 laurate[1] |
| Emulsifier component B: | 5% dilauryl citrate[2] |
| Emulsifier 4: | |
| Emulsifier component A: | 92% polyglyceryl-4 laurate[1] |
| Emulsifier component B: | 8% dilauryl citrate[2] |
| Emulsifier 5: | |
| Emulsifier component A: | 98.5% polyglyceryl-4 laurate[1] |
| Emulsifier component B: | 1.5% disodium lauryl sulfosuccinate[3] |
| Emulsifier 6: | |
| Emulsifier component A: | 98.5% polyglyceryl-3 laurate[4] |
| Emulsifier component B: | 1.5% potassium cetyl phosphate[5] |
| Emulsifier 7: | |
| Emulsifier component A: | 77% polyglyceryl-4 laurate[1] |
| | 19% sorbitan laurate[6] |
| Emulsifier component B: | 4% dilauryl citrate[2] |
| Emulsifier 8: | |
| Emulsifier component A: | 64% polyglyceryl-6 laurate[7] |
| | 29% polyglyceryl-4 laurate[1] |
| Emulsifier component B: | 7% dilauryl citrate[2] |
| Emulsifier 9: | |
| Emulsifier component A: | 49% polyglyceryl-6 laurate[7] |
| | 46% sorbitan laurate[6] |
| Emulsifier component B: | 5% dilauryl citrate[2] |

Emulsifier 10:

| | |
|---|---|
| Emulsifier component A: | 19% polyglyceryl-10 laurate[8]<br>77% sorbitan laurate[6] |
| Emulsifier component B: | 4% dilauryl citrate[2] |

Emulsifier 11:

| | |
|---|---|
| Emulsifier component A: | 94% polyglyceryl-4 laurate[1] |
| Emulsifier component B: | 6% dilauryl citrate[2] |

[1] TEGO ® Care PL 4 (Degussa)
[2] Partly KOH-neutralized diester formed from lauryl alcohol and citric acid
[3] REWOPOL ® SB F 12 P (Degussa)
[4] Polyglyceryl-3 laurate having a degree of esterification of 20% of the OH groups
[5] Amphisol ® K (Roche)
[6] TEGO ® SML (Degussa)
[7] Polyglyceryl-6 laurate having a degree of esterification of 13% of the OH groups
[8] Polyglyceryl-10 laurate having a degree of esterification of 8% of the OH groups Examples of Clear Oil Phases 1-10:

These examples are intended to show in particular the composition of inventive clear oil phases (data in % by weight) which can be processed in a further step at room temperature to give inventive, fine oil-in-water emulsions (see example emulsions 1-10).

| | Clear oil phases | | | | |
|---|---|---|---|---|---|
| | 1 | 2 | 3 | 4 | 5 |
| Emulsifier 2 | | 22.0% | 20.8% | | |
| Emulsifier 3 | 22.0% | | | 22.0% | |
| Emulsifier 5 | | | | | 22.0% |
| isopropyl palmitate | 66.0% | | | 66.0% | 66.0% |
| ethylhexyl palmitate | | | 62.5% | | |
| diethylhexyl carbonate | | 66.0% | | | |
| Euxyl ® K 300[9] | 12.0% | 12.0% | 11.7% | | 12.0% |
| benzyl alcohol | | | | 12.0% | |
| water | | | 5.0% | | |

| | Clear oil phases | | | | |
|---|---|---|---|---|---|
| | 6 | 7 | 8 | 9 | 10 |
| Emulsifier 5 | | | | | |
| Emulsifier 7 | | 23.6% | 22.9% | | |
| Emulsifier 8 | 21.7% | | | | |
| Emulsifier 11 | | | | 23.4% | 23.5% |
| sorbitan octanoate[10] | | | | 1.7% | 2.8% |
| isopropyl palmitate | | | | 35.1% | 35.0% |
| ethylhexyl palmitate | | 70.7% | 68.7% | | |
| C12–15 alkyl benzoate | 65.1% | | | | |
| isohexadecane | | | | 35.1% | |
| Paraffin oil (25 mPas at 30° C.) | | | | | 35.0% |
| phenoxyethanol | | | | | 3.7% |
| Euxyl ® K 300[9] | 12.2% | | 7.4% | 4.7% | |
| Euxyl ® PE 9010[11] | | 5.7% | | | |
| water | 1.0% | | 1.0% | | |

[9] Euxyl ® K 300 (Schülke & Mayr): phenoxyethanol, methylparaben, ethylparaben, propylparaben, butylparaben, isopropylparaben
[10] TEGOTENS ® SD (Degussa)
[11] Euxyl ® PE 9010 (Schülke & Mayr): phenoxyethanol, ethylhexylglycerol Examples of Clear to Transparent Microemulsion-Like Concentrates 1-10:

These examples are intended to show in particular the composition of inventive clear to transparent microemulsion-like concentrates (data in % by weight) which can be processed in a further step at room temperature to give inventive, fine oil-in-water emulsions (see example emulsions 11-20).

| | Microemulsion-like concentrates | | | | |
|---|---|---|---|---|---|
| | 1 | 2 | 3 | 4 | 5 |
| Emulsifier 1 | 14.3% | 13.2% | | | |
| Emulsifier 4 | | | | 9.1% | |
| Emulsifier 6 | | | 8.8% | | |
| Emulsifier 7 | | | | | 12.5% |
| decyl cocoate | | 39.6% | | | |
| ethylhexyl palmitate | 42.9% | | 26.4% | 27.4% | 37.5% |
| Euxyl ® K 300[9] | 7.8% | 7.2% | 4.8% | 8.5% | |
| phenoxyethanol | | | | | 5.0% |
| water | 35.0% | 40.0% | 60.0% | 55.0% | 45.0% |

| | Microemulsion-like concentrates | | | | |
|---|---|---|---|---|---|
| | 6 | 7 | 8 | 9 | 10 |
| Emulsifier 2 | | | | | 14.3% |
| Emulsifier 7 | 13.2% | | | | |
| Emulsifier 9 | | 14.3% | | | |
| Emulsifier 10 | | | 18.6% | | |
| Emulsifier 11 | | | | 14.3% | |
| diethylhexyl carbonate | | | | 42.8% | 32.2% |
| ethylhexyl palmitate | | 42.9% | 55.9% | | |
| cetearyl isononanoate | 39.6% | | | | |
| cyclopentasiloxane | | | | | 10.7% |
| Euxyl ® K 300[9] | | 7.8% | 10.5% | | |
| phenoxyethanol | | | | | 7.8% |
| benzyl alcohol | 7.2% | | | | |
| capryl glycol[12] | | | | 2.9% | |
| water | 40.0% | 35.0% | 15.0% | 40.0% | 35.0% |

[12] Dermosoft ® Octiol (Dr. Straetmans) (1,2-octanediol)

Example Emulsions 1-24:

Emulsions 1-24 are intended to illustrate the structure of inventive emulsions by way of example (data in % by weight).

Emulsions 1-10 were prepared by pouring the clear oil phases (examples 1-10 (see above)) into water at room temperature using a simple manual stirrer apparatus.

Emulsions 11-20 were likewise prepared at room temperature by diluting the clear to transparent microemulsion-like concentrates (corresponding examples 1-10 (see above)) using a simple manual stirrer apparatus.

Example emulsions 21-24 are based on the clear oil phases 2 and 3 and were prepared therefrom by diluting with mixing. By way of example, water-soluble assistants and additives were added to the water phase.

In some examples, perfume was added in accordance with the invention as an assistant and additive, which was dissolvable immediately in the appropriate amounts in the clear oil phases or in clear to transparent microemulsion-like concentrates.

All example emulsions are low in viscosity, have fine distribution and have long-term stability.

| | Example emulsions | | | | |
|---|---|---|---|---|---|
| | 1 | 2 | 3 | 4 | 5 |
| Emulsifier 2 | | 1.25% | 1.25% | | |
| Emulsifier 3 | 1.25% | | | 1.25% | |
| Emulsifier 5 | | | | | 1.25% |
| isopropyl palmitate | 3.75% | | | 3.75% | 3.75% |
| ethylhexyl palmitate | | | 3.75% | | |
| diethylhexyl carbonate | | 3.75% | | | |

-continued

| | 1 | 2 | 3 | 4 | 5 |
|---|---|---|---|---|---|
| Euxyl ® K 300[9)] | 0.7% | 0.7% | 0.7% | | 0.7% |
| benzyl alcohol | | | | 0.7% | |
| perfume | | | | | 0.2% |
| water | 94.3% | 94.3% | 94.3% | 94.3% | 94.1% |

| | Example emulsions | | | | |
|---|---|---|---|---|---|
| | 6 | 7 | 8 | 9 | 10 |
| Emulsifier 7 | | 1.25% | 2.5% | | |
| Emulsifier 8 | 1.25% | | | | |
| Emulsifier 11 | | | | 4.0% | 5.0% |
| sorbitan octanoate[10)] | | | | 0.3% | 0.6% |
| isopropyl palmitate | | | | 6.0% | 7.5% |
| ethylhexyl palmitate | | 3.75% | 7.5% | | |
| C12–15 alkyl benzoate | 3.75% | | | | |
| isohexadecane | | | | 6.0% | |
| Paraffin oil (25 mPas at 30° C.) | | | | | 7.5% |
| phenoxyethanol | | | | | 0.8% |
| Euxyl ® K 300[9)] | 0.7% | | 0.8% | 0.8% | |
| Euxyl ® PE 9010[11)] | | 0.3% | | | |
| perfume | 0.2% | 0.2% | 0.2% | | |
| water (total) | 94.1% | 94.5% | 89.0% | 82.9% | 78.6% |

| | Example emulsions | | | | |
|---|---|---|---|---|---|
| | 11 | 12 | 13 | 14 | 15 |
| Emulsifier 1 | 1.25% | 1.25% | | | |
| Emulsifier 4 | | | | 0.75% | |
| Emulsifier 6 | | | 1.25% | | |
| Emulsifier 7 | | | | | 1.25% |
| decyl cocoate | | 3.75% | | | |
| ethylhexyl palmitate | 3.75% | | 3.75% | 2.25% | 3.75% |
| phenoxyethanol | | | | | 0.5% |
| Euxyl ® K 300[9)] | 0.7% | 0.7% | 0.7% | 0.7% | |
| perfume | 0.2% | 0.2% | 0.2% | | |
| water (total) | 94.1% | 94.1% | 94.1% | 96.3% | 94.3% |

| | Example emulsions | | | | |
|---|---|---|---|---|---|
| | 16 | 17 | 18 | 19 | 20 |
| Emulsifier 2 | | | | | 1.25% |
| Emulsifier 7 | 1.25% | | | | |
| Emulsifier 9 | | 1.25% | | | |
| Emulsifier 10 | | | 1.25% | | |
| Emulsifier 11 | | | | 2.5% | |
| diethylhexyl carbonate | | | | 7.5% | 2.81% |
| ethylhexyl palmitate | | 3.75% | 3.75% | | |
| cetearyl isononanoate | 3.75% | | | | |
| cyclopentasiloxane | | | | | 0.94% |
| Euxyl ® K 300[9)] | | 0.7% | 0.7% | | |
| phenoxyethanol | | | | | 0.7% |
| benzyl alcohol | 0.7% | | | | |
| capryl glycol[12)] | | | | 0.5% | |
| perfume | 0.2% | 0.2% | 0.2% | | |
| water (total) | 94.1% | 94.1% | 94.1% | 89.5% | 94.3% |

| | Example emulsions | | | |
|---|---|---|---|---|
| | 21 | 22 | 23 | 24 |
| Emulsifier 2 | 1.25% | 1.25% | 1.25% | 1.25% |
| ethylhexyl palmitate | 3.75% | | 3.75% | |
| diethylhexyl carbonate | | 3.75% | | 3.75% |
| Euxyl ® K 300[9)] | 0.7% | 0.7% | 0.7% | 0.7% |
| ethanol | 3.0% | | | |
| glycerol | | 3.0% | | |
| panthenol | | | 0.5% | |
| creatine | | | | 0.25% |
| water (total) | 91.3% | 91.3% | 93.8% | 94.05% |

Particle Size Determination by Dynamic Light Scattering:

By way of example for the extremely fine degree of dispersion of the inventive emulsions, the particle size of individual example emulsions was characterized with the aid of dynamic light scattering.

Dynamic light scattering is based on the analysis of the variations of the scattered light intensity of diffusing particles in solution. For dilute solutions, it is possible thereby to determine the coefficient of diffusion of the particles in solution, which can be converted via the Stokes-Einstein equation to a mean hydrodynamic radius $<r_h>$ of the particles (here: emulsion droplets).

In the present case, the example emulsions mentioned were diluted by a factor of 10 with demineralized water and characterized with the aid of a dynamic light scattering instrument from Malvern Instruments (HPPS 3.1) at 25° C. In each case, the mean values of three measurements are reported with 100 seconds of measurement time in each case.

| Example emulsion | $<r_h>$ in nm |
|---|---|
| 2 | 55 |
| 3 | 60 |
| 6 | 75 |
| 8 | 75 |
| 18 | 110 |
| 20 | 45 |

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed is:

1. A prolonged-stability, low-viscosity, fine oil-in-water emulsion comprising:
    A) an emulsifier mixture consisting of:
        a) 75 to 99.5% by weight of at least one nonionic primary emulsifier selected from the group consisting of polyglyceryl laurates, and mixtures of polyglyceryl laurates with sorbitan laurates, and
        b) 0.5 to 25% by weight of at least one secondary emulsifier containing one or more acid functions and selected from the group consisting of partly neutralized or neutralized citric acid partial esters whose hydrophobic radicals each contain from 10 to 18 carbon atoms;
    B) one or more cosurfactants; and
    C) one or more oils,
    with the proviso that the water phase content of the emulsion is 70% by weight or greater based on the overall emulsion, and said oil-in-water emulsion is free of polyethylene glycol (PEG).

2. The oil-in-water emulsion as claimed in claim 1, wherein said water phase content is from 80 to 99% by weight.

3. The oil-in-water emulsion as claimed in claim 1, wherein said emulsifier mixture (A), cosurfactants (B) and oils (C) are present in proportions by weight of from 10 to 30 (A), from 3 to 20 (B) and from 50 to 87 (C).

4. The oil-in-water emulsion as claimed in claim 1, wherein the nonionic primary emulsifier component (a) consists of a mixture of from 25 to less than 100% by weight of polyglyceryl laurates and from greater than 0 to 75% by weight of sorbitan laurates.

5. The oil-in-water emulsion as claimed in claim 1, wherein said at least one cosurfactant (B) is selected from the group consisting of n-pentanol, n-hexanol, 1,2-hexanediol, 1,2-heptanediol and 1,2-octanediol.

6. The oil-in-water emulsion as claimed in claim 1, wherein said at least one cosurfactant (B) is aromatic.

7. The oil-in-water emulsion as claimed in claim 6, wherein the aromatic cosurfactants (B) include phenoxyethanol, benzyl alcohol, alkylparaben esters alone or in mixtures with one another and/or customary preservatives.

8. The oil-in-water emulsion as claimed in claim 1, wherein the oils (C) are cosmetic ester or ether oils.

9. The oil-in-water emulsion as claimed in claim 1, wherein the oils (C) are at least one compound selected from the group consisting of ethylhexyl palmitate, ethylhexyl stearate, decyl cocoate, diethylhexyl carbonate, dioctyl carbonate, cetearyl ethylhexanoate, decyl oleate, isocetyl palmitate, cetearyl isononanoate, hexyl laurate, isopropyl isononanoate, isopropyl stearate, isopropyl palmitate, isopropyl myristate, isopropyl laurate, C12-15 alkyl benzoate, dicaprylyl ether, mineral oil, isohexadecane, cyclopentasiloxane, octyldodecanol and mixtures of these compounds.

10. An oil phase comprising:
    A) an emulsifier mixture consisting of:
       a) 75 to 99.5% by weight of at least one nonionic primary emulsifier selected from the group consisting of polyglyceryl laurates, and mixtures of polyglyceryl laurates with sorbitan laurates, and
       b) 0.5 to 25% by weight of at least one secondary emulsifier containing one or more acid functions and selected from the group consisting of partly neutralized or neutralized citric acid partial esters whose hydrophobic radicals each contain from 10 to 18 carbon atoms;
    B) one or more cosurfactants;
    C) one or more oils; and
    D) from 0 to less than 10% by weight, based on the overall oil phase, of one or more polar solubilizers, wherein said oil phase is free of polyethylene glycol (PEG).

11. The oil phase as claimed in claim 10, which is homogeneous and clear.

12. A process for preparing oil-in-water emulsions, which comprises adjusting an oil phase as claimed in claim 10 to a total water phase content of 70% by weight or greater with an appropriate water phase.

13. A clear to transparent microemulsion-like concentrate comprising:
    A) an emulsifier mixture consisting of:
       a) 75 to 99.5% by weight of at least one nonionic primary emulsifier selected from the group consisting of polyglyceryl laurates, and mixtures of polyglyceryl laurates with sorbitan laurates, and
       b) 0.5 to 25% by weight of at least one secondary emulsifier containing one or more acid functions and selected from the group consisting of partly neutralized or neutralized citric acid partial esters whose hydrophobic radicals each contain from 10 to 18 carbon atoms;
    B) one or more cosurfactants; and
    C) one or more oils,
    with the proviso that the total water phase content of the microemulsion-like concentrate is from 10 to less than 70% by weight, based on the overall concentrate and said microemulsion-like concentrate is free of polyethylene glycol (PEG).

14. A process for preparing oil-in-water emulsions, which comprises adjusting clear to transparent microemulsion-like concentrates as claimed in claim 13 to a total water phase content of 70% by weight or greater with an appropriate water phase.

15. A formulation comprising an oil-in-water emulsion as claimed in claim 1.

16. Impregnated wipes or in sprayable formulations for face- and bodycare, babycare, sun protection, makeup removers, antiperspirants/deodorants comprising the oil-in-water emulsion of claim 1.

* * * * *